United States Patent
Li et al.

(10) Patent No.: US 8,241,212 B2
(45) Date of Patent: *Aug. 14, 2012

(54) CARDIAC SIGNAL DISPLAY AND EVENT DETECTION USING MULTIRESOLUTION Z-SCORE TRANSFORM

(75) Inventors: Dan Li, Shoreview, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 14 days.

This patent is subject to a terminal disclaimer.

(21) Appl. No.: 12/510,927

(22) Filed: Jul. 28, 2009

(65) Prior Publication Data

US 2009/0287068 A1 Nov. 19, 2009

Related U.S. Application Data

(62) Division of application No. 11/459,588, filed on Jul. 24, 2006, now Pat. No. 7,572,232.

(51) Int. Cl.
*A61B 5/00* (2006.01)
*A61B 5/04* (2006.01)
(52) U.S. Cl. .......................... 600/301; 600/523; 600/509
(58) Field of Classification Search .............. 607/17–18, 607/30, 20; 600/509–510, 513, 523, 525
See application file for complete search history.

(56) References Cited

U.S. PATENT DOCUMENTS

| | | | |
|---|---|---|---|
| 4,201,224 A | 5/1980 | John | |
| 4,913,160 A | 4/1990 | John | |
| 5,357,428 A * | 10/1994 | Stone, Jr. | 600/372 |
| 6,066,163 A | 5/2000 | John | |
| 6,389,308 B1 * | 5/2002 | Shusterman | 600/509 |
| 6,463,328 B1 | 10/2002 | John | |
| 6,547,746 B1 | 4/2003 | Marino | |
| 6,697,660 B1 | 2/2004 | Robinson | |
| 6,778,852 B2 * | 8/2004 | Galen et al. | 600/523 |
| 7,068,275 B2 | 6/2006 | Nakamura et al. | |
| 7,089,927 B2 | 8/2006 | John et al. | |
| 7,184,150 B2 | 2/2007 | Quadling et al. | |
| 7,572,232 B2 | 8/2009 | Li et al. | |
| 2003/0233250 A1 | 12/2003 | Joffe et al. | |
| 2004/0079372 A1 * | 4/2004 | John et al. | 128/204.18 |
| 2004/0122486 A1 | 6/2004 | Stahmann et al. | |
| 2004/0167423 A1 | 8/2004 | Pillon et al. | |
| 2005/0010106 A1 * | 1/2005 | Lang et al. | 600/425 |

(Continued)

OTHER PUBLICATIONS

"U.S. Appl. No. 11/459,588, Non-Final Office Action mailed Oct. 9, 2008", 9 pgs.

(Continued)

*Primary Examiner* — Niketa Patel
*Assistant Examiner* — Catherine Voorhees
(74) *Attorney, Agent, or Firm* — Schwegman, Lundberg & Woessner, P.A.

(57) ABSTRACT

A system comprising a medical device including a processor and a Z-score transformation (ZST) module. The system also includes a display in communication with the processor. The processor is adapted to receive sensor data obtained from at least first and second sensors adapted to produce a time-varying physiologic electrical sensor signal. At least one of the first and second sensors is implantable. The ZST module calculates a ZST for the sensor data received from the first sensor and a ZST for the sensor data received from the second sensor. The display is adapted to display the ZSTs in visual correspondence with each other over time.

20 Claims, 7 Drawing Sheets

U.S. PATENT DOCUMENTS

| | | |
|---|---|---|
| 2005/0119547 A1 | 6/2005 | Shastri et al. |
| 2005/0144042 A1 | 6/2005 | Joffe et al. |
| 2005/0254702 A1 | 11/2005 | Era |
| 2005/0277912 A1 | 12/2005 | John |
| 2006/0036152 A1 | 2/2006 | Kozel |
| 2006/0217781 A1 | 9/2006 | John |
| 2006/0258947 A1* | 11/2006 | Olson .......................... 600/523 |
| 2007/0208263 A1 | 9/2007 | John et al. |
| 2007/0213599 A1 | 9/2007 | Siejko et al. |
| 2007/0276270 A1 | 11/2007 | Tran |
| 2008/0021337 A1 | 1/2008 | Li et al. |
| 2008/0081961 A1 | 4/2008 | Westbrook et al. |

OTHER PUBLICATIONS

"U.S. Appl. No. 11/459,588, Notice of Allowance mailed Apr. 6, 2009", 9 pgs.

"U.S. Appl. No. 11/459,588, Response filed Feb. 9, 2009 to Non-Final Office Action mailed Oct. 9, 2008", 9 pgs.

"U.S. Appl. No. 11/459,588, Response filed Sep. 4, 2008 to Restriction Requirement mailed Aug. 5, 2008", 10 pgs.

"U.S. Appl. No. 11/459,588, Restriction Requirement mailed Aug. 5, 2008", 7 pgs.

* cited by examiner

CARDIAC SIGNAL DISPLAY AND EVENT DETECTION USING MULTIRESOLUTION Z-SCORE TRANSFORM

CROSS REFERENCE TO RELATED APPLICATIONS

This patent application is a divisional application of U.S. patent application Ser. No. 11/459,588 filed Jul. 24, 2006, now issued as U.S. Pat. No. 7,572,232. The specification of which is incorporated herein by reference in its entirety.

TECHNICAL FIELD

The field generally relates to implantable medical devices and, in particular, but not by way of limitation, to systems and methods for interpreting data collected from physiologic sensors.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. In general, the sensors convert sensed internal parameters into electrical signals. The electrical signals monitored within the patient and the electrical signals from the sensors can be quantized by analog-to-digital converters and stored in the IMD as data. Other examples of implantable medical devices include implantable diagnostic devices, implantable insulin pumps, devices implanted to administer drugs to a patient, or implantable devices with neural stimulation capability.

IMDs are able to communicate with external devices using wireless communication methods. The external devices are often external programmers that use wireless communication links to change performance parameters in the implantable device. The IMD also wirelessly transmits stored data obtained from sensors to an external device. The external device may then display the collected data on a computer screen display or a strip chart recorder.

As technology used in IMDs advances, the devices are able to collect data from multiple sensors at multiple locations. They also detect events occurring from such multiple sources. Because the data may be collected from different types of sensors, the data may be dissimilar from one sensor to the next. Also, the data may be collected at different times and/or sampling rates. The large amount of data coming from various sources complicates the task of reconstructing the information for a display while preserving the correct relationships among the data.

SUMMARY

This document discusses, among other things, systems and methods for interpreting data collected from physiologic sensors. A system example includes a medical device that includes a processor and a Z-score transformation (ZST) module included in the processor. The system also includes a display in communication with the processor. The processor is adapted to receive sensor data obtained from at least first and second sensors adapted to produce a time-varying physiologic electrical sensor signal. At least one of the first and second sensors is implantable. The ZST module calculates a ZST for the sensor data received from the first sensor and a ZST for the sensor data received from the second sensor. The display is adapted to display the ZSTs in visual correspondence with each other over time.

A method example includes sensing at least one time-varying physiologic implantable sensor signal, sampling the sensor signal to obtain sensor data, calculating a multi-resolution ZST of the sensor data, and displaying a resulting multi-resolution ZST. A multi-resolution ZST is calculated by calculating a ZST over a first data segment length of a sensor signal to obtain a first resolution ZST region, and calculating at least a second ZST over a second data segment length of the sensor signal to obtain at least a second resolution ZST region.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

This document discusses systems and methods for interpreting data collected from physiologic sensors. In a multi-sensor multi-modal physiologic detection system, a large amount of data is acquired from a variety of sensors and other sources. Such a system should be able to transmit, monitor, replay, and trend signals from different sources, and detect events of interest from the signals.

A Z-score transformation of a variable X having mean μ, standard deviation σ, and variance σ² is defined as $$Z_X := (X - \mu)/\sigma \quad (1)$$

and indicates how far and in what direction X deviates from its mean, expressed in units of its standard deviation. Because $Z_X$ is zero-mean and unit-variance regardless of the statistical property of X, ZST can be very useful in such a system as it makes it easier to compare the relative standings of parameters from distributions with different means and/or different variances, to identify quickly the correlation among different signals, and to recognize the outstanding spatial or temporal regions where an event of interest may occur. ZST with multiple resolutions further facilitates quick recognition of the outstanding trend and/or the inter-signal relationship.

Figure 1:
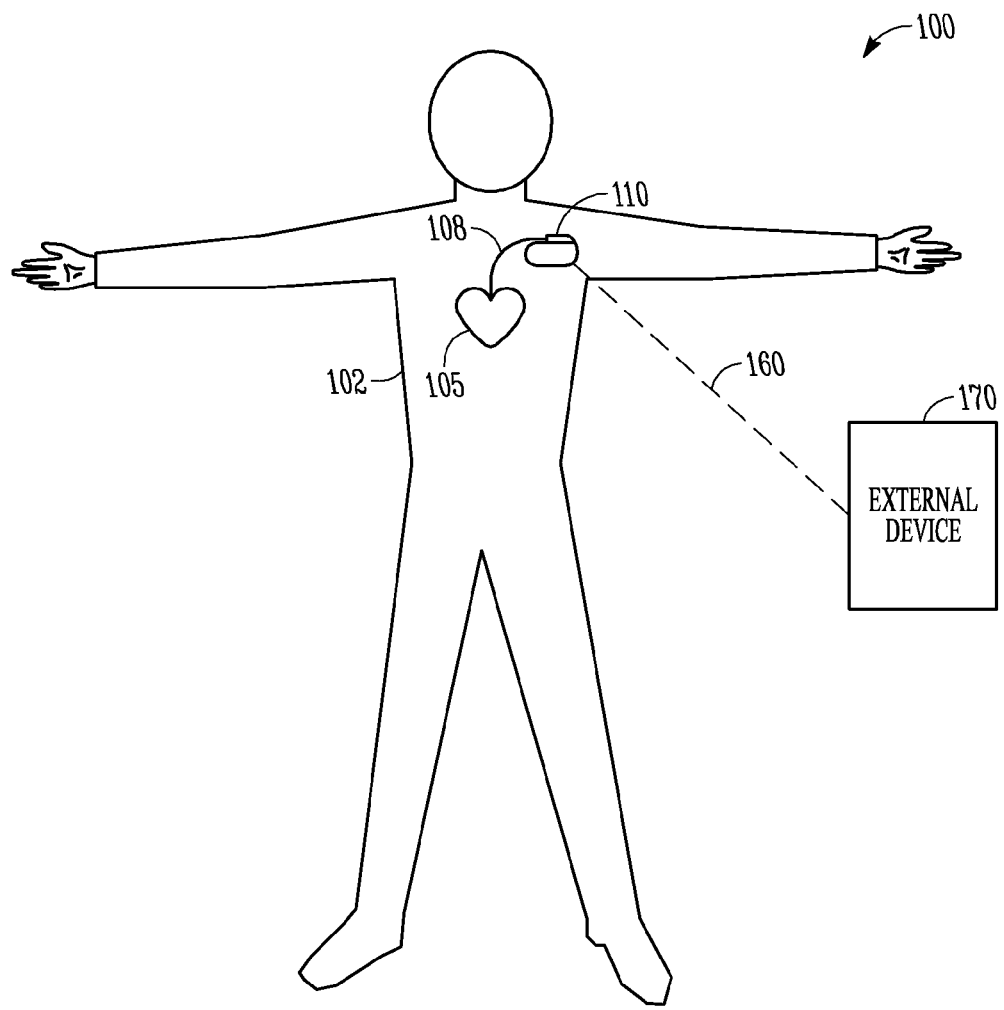
FIG. 1 is a block diagram of portions of a system that uses an implantable medical device (IMD).

FIG. 1 is a block diagram of portions of a system 100 that uses an implantable medical device (IMD) 110. As one example, the system 100 shown is used to treat a cardiac arrhythmia. The IMD 110 typically includes an electronics unit coupled by a cardiac lead 108, or additional leads, to a heart 105 of a patient 102, or otherwise associated with the heart 105. Examples of IMD 110 include, without limitation, a, pacemaker, a cardioverter, a defibrillator, a cardiac resynchronization therapy (CRT) device, and other cardiac monitoring and therapy delivery devices, including cardiac devices that include or work in coordination with neuro-stimulating devices, drug pumps, or other therapies. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing intrinsic or other electrical activity of the heart 105.

Figure 2:
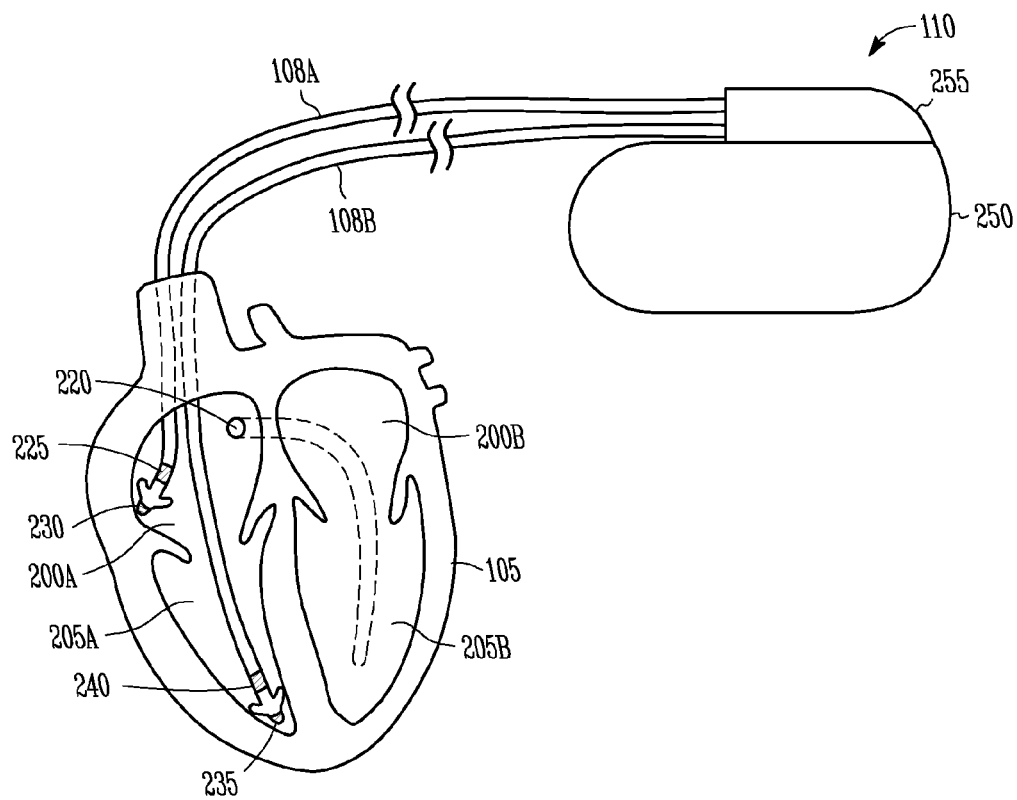
FIG. 2 illustrates an IMD coupled by one or more leads to a heart.

FIG. 2 illustrates an IMD 110 coupled by one or more leads 108A, 108B to heart 105. Heart 105 includes a right atrium 200A, a left atrium 200B, a right ventricle 205A, a left ventricle 205B, and a coronary sinus 220 extending from right atrium 200A. Leads 108A, 108B may include electrodes (electrical contacts, such as ring electrode 225 and tip electrode 230) disposed in a ventricle 205A of heart 105 for sensing signals, or delivering pacing therapy, or both, to the ventricle 205A. Leads 108A, 108B may also include one or more electrodes for placement in the right atrium 200A, such as ring electrode 235 and ring electrode 240, for sensing electrical cardiac signals, delivering pacing therapy, or both sensing signals and delivering pacing therapy. Sensing and pacing allows the IMD 110 to adjust timing of the chamber contractions. For example, IMD 110 can adjust the timing of ventricular contractions with respect to the timing of atrial contractions delay by sensing a contraction in the right atrium 200A and pacing the right ventricle 205A at the desired AV delay time. The IMD also includes an electrode formed on the IMD can 250, and a header electrode formed on the IMD header 255.

IMD optionally also includes additional leads and electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Optionally, lead 108 includes two leads containing two electrodes each. In an example, a first lead includes a tip electrode located in the apex of the right ventricle 205A and a first ring electrode located proximal to the tip electrode. A second lead includes a tip electrode located in the right atrium 200A and a ring electrode located in the right atrium 200A proximal to the tip electrode.

Optionally, IMD 110 includes an additional cardiac lead that includes ring electrodes for placement in a coronary vein extending along a wall of the left ventricle 205B. A lead placed in the left ventricle 205B and a lead placed in the right ventricle 205A may be used to optionally provide resynchronization therapy to the heart 105.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes.

Figure 3:
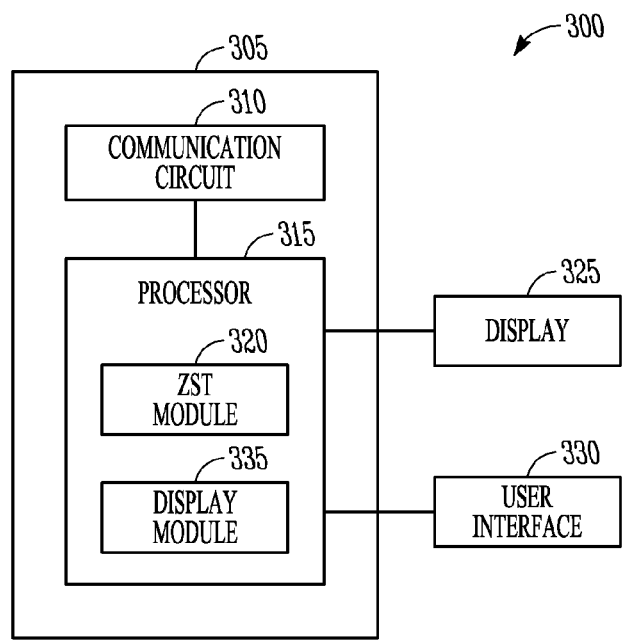
FIG. 3 is a block diagram of portions of an example of a system for interpreting data collected from physiologic sensors and other sources.

FIG. 3 is a block diagram of portions of an example of a system 300 for interpreting data collected from physiologic sensors and other sources. The system 300 includes a medical device 305. The medical device 305 includes a processor 315 that receives sensor data obtained from at least first and second sensors. The term processor may include a digital signal processor, ASIC, microprocessor, or other type of processor. In some examples, the medical device 305 is an external medical device that communicates with an implantable medical device (IMD) using communication circuit 310. In some examples, the medical device 305 is an IMD programmer. In some examples, the medical device 305 is part of a patient management system, which may include a remote server that communicates over a communication network, such as a mobile phone network, or a computer network with a local external interface to an implantable or personal ambulatory medical device. In some examples, the medical device 305 includes a server in communication with a network such as a hospital computer network or the internet.

Each sensor produces a time-varying physiologic electrical sensor signal. At least one of the sensors is an implantable sensor. A non-exhaustive list of examples of implantable sensors include an accelerometer, an implantable pressure sensor, an intracardiac impedance sensing circuit, a transthoracic impedance sensing circuit, an electrical cardiac signal sensing circuit, a blood pressure sensor, and a heart sound sensor. Examples of external sensors include, among other things, an external ECG circuit and an external blood pressure sensor. The external sensors may be coupled to the medical device 305 or to a second external device in communication with the first medical device 305.

The processor 315 includes a Z-score transformation (ZST) module 320. The ZST module 320 includes software, hardware, firmware or any combination of software, hardware, and firmware. The ZST module 320 calculates a ZST for the sensor data received from the first sensor and a ZST for the sensor data received from the second sensor. The system 300 also includes a display 325 in communication with the processor 315 to display the ZSTs in visual correspondence with each other over time. In some examples, the display 325 is coupled to the processor 315, such as with an IMD programmer, or can be in communication with the processor 315 over a network, such as in a patient management system. For example, the processor 315 can be included in a remote server system in communication with a second device over a network, and the second device includes the display 325.

Figure 4:
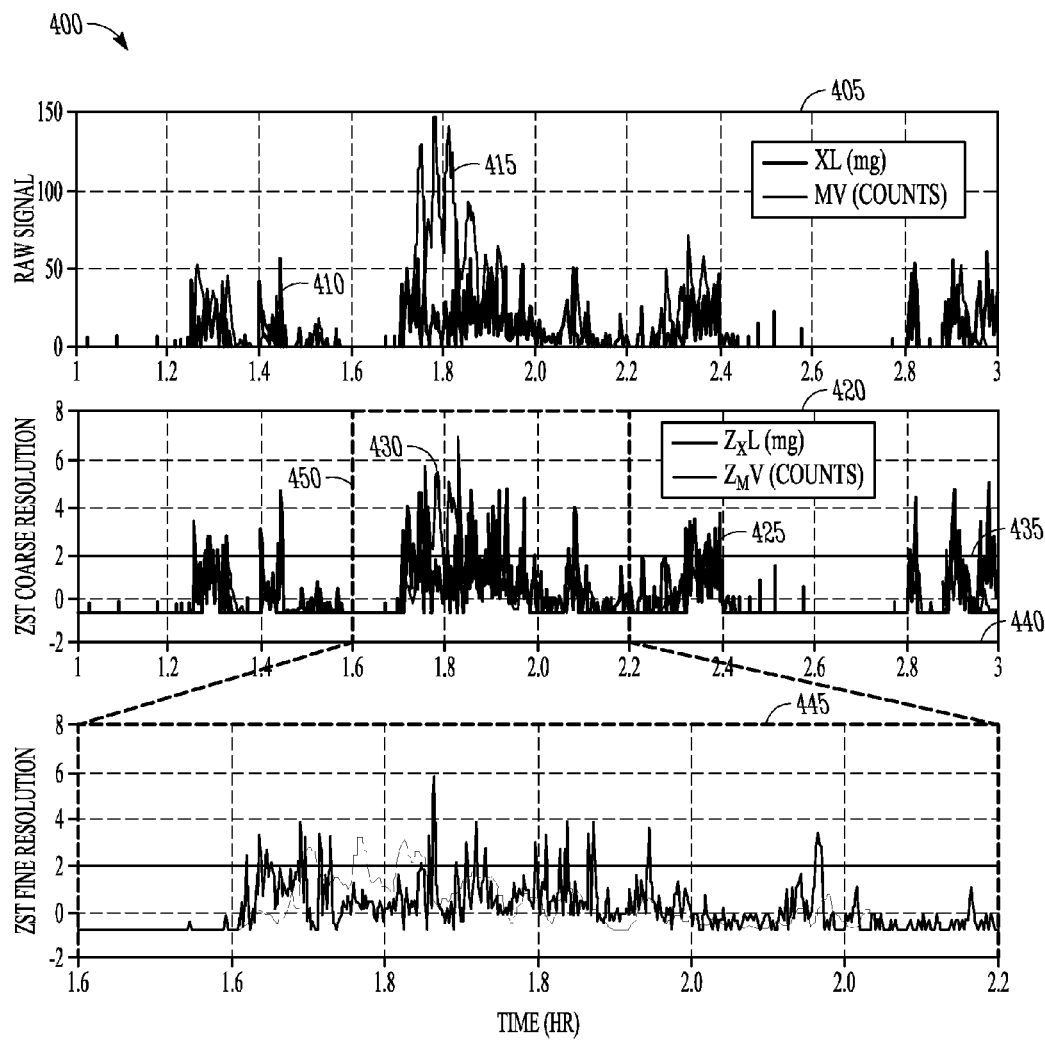
FIG. 4 shows graphs of an example of displaying Z-score transformations (ZSTs) for sensor data.

FIG. 4 shows graphs 400 of an example of displaying ZSTs for sensor data. The top graph 405 displays sensor data 410 (darker line) received from an implantable accelerometer (XL) sensor and sensor data 415 (lighter line) received from an implantable transthoracic impedance sensor used to measure respiration, such as minute ventilation (MV). The accelerometer produces an electrical sensor signal representative of motion or activity level of a patient. The transthoracic impedance sensor produces an electrical sensor signal representative of breathing of the patient and is useful to detect changes in breathing, such as due to exercise, stress, and emotion.

Typically, the "raw" data from sensors is recorded and played back for display. Often it can be difficult for a caregiver to visually inspect the display and quickly recognize the relative importance of the sensor outputs or to recognize any exceptional value of one or both sensors. The scale of the raw data obtained from the two sensors may differ and the sensors may have different signal statistics as well, such as a different mean, variance, or probability distribution. In the top graph 405 for example, the scale of the XL sensor data is in milli-g's (where 1 g=acceleration of gravity) and the scale of the MV data is in counts. The middle graph 420 displays the Z-score transform (ZST) for the XL data ($Z_{XL}$) 425 and the ZST for the MV data ($Z_{MV}$) 430. The ZSTs normalize the data from the sensors to the same scale so that the comparison becomes more meaningful. The ZST is typically expressed in units of standard deviations (SD). The normal value range of the ZST can be defined as the mean±2 SD. The two horizontal bars 435, 440 indicate the normal value range. The region outside the normal value range is sometimes called the outstanding region to indicate sample values that are away from the mean.

The ZST for a time series of sampled data x(n) can be computed on a segment-by-segment basis. This can sometimes be called a segmental ZST. The system 300 acquires data from the sensors. In some examples, the data is collected by the IMD and communicated to the medical device 305. The data can be collected and communicated in real time, or the IMD can collect the data, store it in an IMD memory, and communicate the data at a later time. In some examples, the medical device 305 is part of a patient management system and includes a remote server. The data is communicated by the IMD or a second external device to the remote server. T-hours of data is collected and stored. The ZST of that T-hour data segment is performed by the ZST module 320 and displayed, such as in graph 420. The next segment is then processed. In some examples, the ZST module 320 automatically updates a ZST calculation when new sampled sensor data becomes available from a sensor.

Segmental ZST is affected by the size of the data segment from which the sample mean µ and variance $\sigma^2$ are computed. For the same number of data points, a longer data segment will yield a lower-resolution estimate of µ and $\sigma^2$, and conversely, a shorter data segment will yield a higher-resolution estimate of µ and $\sigma^2$. A multi-resolution ZST can be conceptualized as the calculation of ZSTs over multiple segment lengths T of the data. This can be seen in the bottom two graphs 420 and 445 of FIG. 4. Graph 445 is an expanded view of the data segment 450 in graph 420 (shown by the broken line). If a ZST is calculated over the segment shown in graph 445 (shorter T) using the same number of data points as is used to calculate a ZST for the entire graph 420 (longer T), µ and $\sigma^2$ for the bottom graph 445 will have a higher resolution, and will therefore reflect more of the small changes shown in graph 445 that are not apparent in graph 420.

In some examples, the ZST module 320 is adapted to determine a ZST having a first resolution for a first segment of sensor data obtained from a sensor, and to determine a ZST having a second resolution for a second segment of sensor data obtained from the sensor. In some examples, the first segment is included in a different segment of sensor data than the second segment. In some examples, the first and second data segment is included in the same data segment.

In some examples, a multi-resolution ZST is determined by the ZST module 320 automatically when it is determined that a ZST is outside of a predetermined normal range. For example, in graph 420, the segment 450 includes an outstanding region having a Z score that exceeds two, and the ZST module automatically calculates a higher resolution ZST over the segment 450. The multi-resolution ZST may be calculated when the ZST has a predetermined threshold number of points outside of the normal range.

In some examples, a multi-resolution ZST is determined interactively. Returning to FIG. 3, the system 300 includes a user interface 330 in communication with the processor 315. Examples of a user interface 330 include without limitation, a computer mouse, a keyboard, a touch-screen, or a graphical user interface (GUI). A ZST can be first calculated and displayed for the first segment under a coarse resolution $T_0$ designated by the user. The ZST module 320 then calculates a ZST over the second segment in response to a signal received through the user interface 330. An example is shown in the bottom two graphs 420 and 445 of FIG. 4. The user selects a region of interest 450 in the first segment.

In response to the user's selection, the ZST module 320 automatically calculates and displays the ZST of the interest region 450 under a finer resolution $T_1$, where $T_1 < T_0$. Graph 445 is the expanded view of the area of interest 450 with greater resolution. This can be viewed as "zooming in" on an indicated area of interest. A general multi-resolution ZST can be computed using the resolutions $\{T_0/2^i\}_{i=1 \sim N}$, where $T_0$ is the initial coarse resolution, i.e. i resolutions or levels are calculated for the region of interest 450 based on the user's selection.

Figure 5:
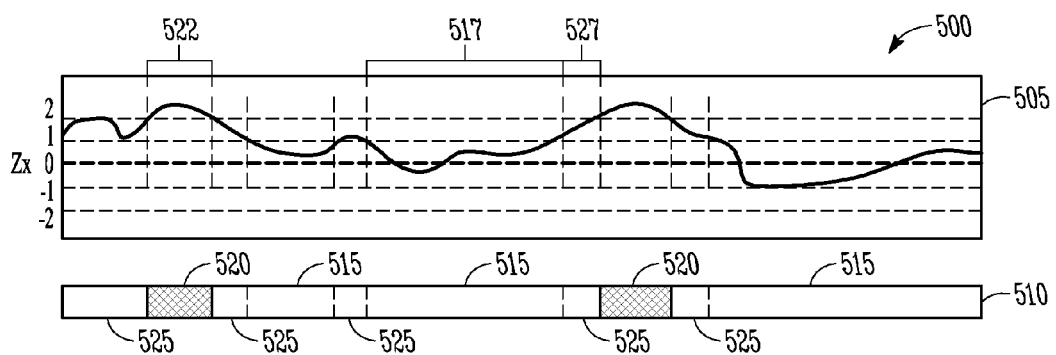
FIG. 5 shows an example of a display of a graph of a ZST of a sensor signal and a color-coded region.

In some examples, the display 325 is a color display and the processor 315 includes a display module 335. The regions of the ZST are divided based on whether a region is within a predetermined value range (e.g., ±1SD) or is outside the predetermined value range. FIG. 5 shows an example of a display 500 of a graph 505 of a ZST of a sensor signal and a color-coded region 510 to indicate different value regions of Z scores. The display module 335 assigns a first display color-code 515 to one or more regions 517 of the ZST that are within the range $|Z_x|<1SD$, assigns a second display color-code 525 to one or more regions 527 of the ZST that are within the range $1SD<|Z_x|<2SD$, and assigns a third display color-code 520 to one or more regions 522 of the ZST that are outside the range $|Z_x|>2SD$. More than three ranges may be used. In some examples, only two ranges are used: a first color-code to indicate that the ZST is within a predetermined normal value range (e.g., within ±2SD) and a second color-code to indicate that the ZST is outside the predetermined normal value range (i.e., in an outstanding region). A ZST may have to have a threshold number of points outside of a value range before a second region is identified and a color code assigned.

Figure 6:
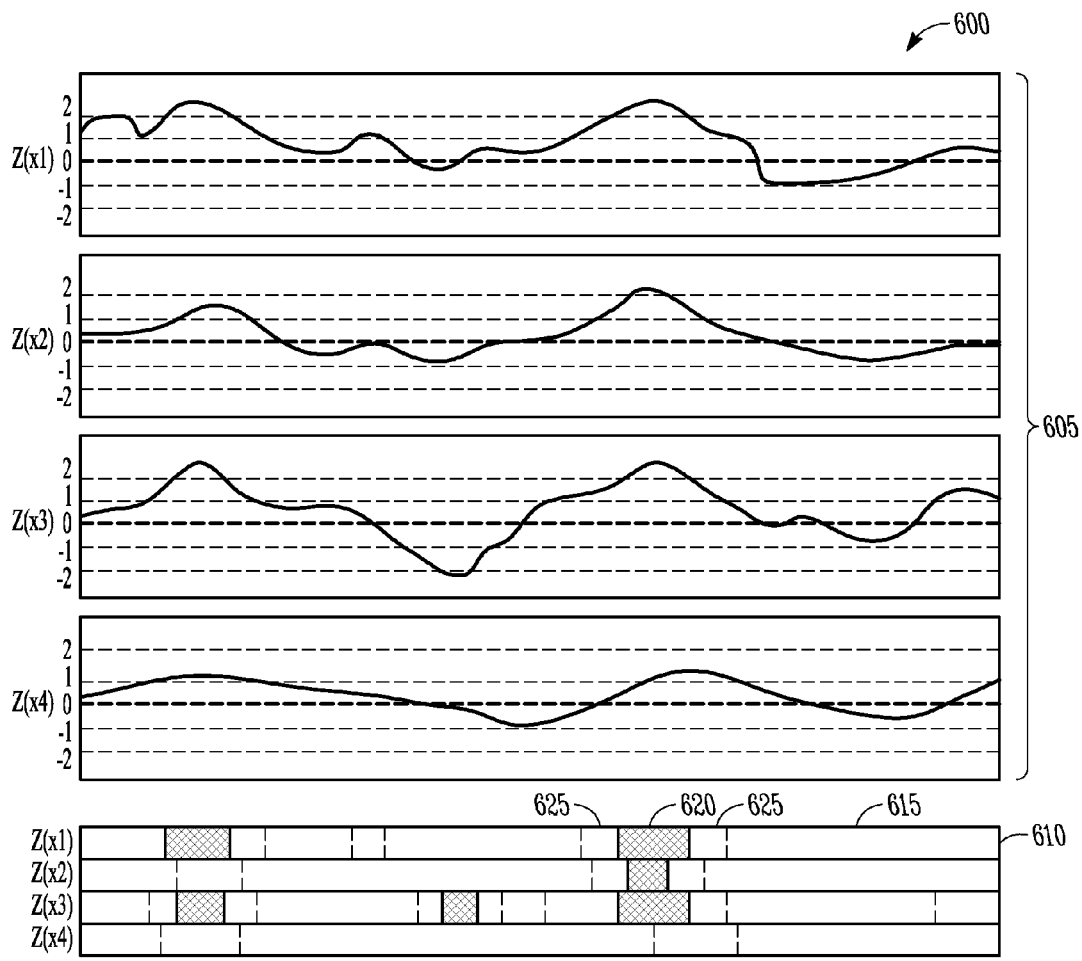
FIG. 6 shows an example of a display of graphs of multi-resolution ZSTs obtained from signals from four sensors and a color map.

FIG. 6 shows an example of a display 600 of graphs 605 of ZSTs obtained from signals from four sensors and a color map 610. The sensor signals may have different scales with respect to time and/or data. The ZST module 320 calculates the ZSTs. The display module 335 assigns color codes 615, 625, and 620 to regions having Z-scores where $|Z_x|<1$, $1<|Z_x|<2$, and $|Z_x|>2$, respectively, to form the color map 610. In some examples, the display module 335 displays different combinations of the ZSTs according to input received from the user interface 330. The graphs 605 of the four ZSTs of sensor data may be a subset selected by a user of the set of sensors for which data was obtained. Or a user can select a subset of the four ZSTs shown using the user interface 330.

In some examples, the display module 335 assigns a first display color-code to a ZST region having a first resolution and a second display color-code to a ZST region having a second resolution. In some examples, the color-codes are displayed on a color map region that is separate from the ZST graph, such as region 510 in FIG. 5. In some examples, color-codes are displayed on the graph 505 of data, although this makes it more difficult to notice the different color regions. The display module 335 assigns a first display color-code to one or more regions of the ZST having a first resolution and a second color-code to one or more regions of the ZST region having a second resolution. If there are i resolutions calculated for the ZST, the display module can assign i color-codes to indicate the regions.

In some examples, the ZST module 320 calculates multi-resolution ZSTs for sensor data obtained from a plurality of sensor signals. One sensor signal may have a different scale from one or more of the other sensor signals with respect to time, or with respect to the data, or with respect to both time and data. The display module 335 assigns color-codes to regions of the ZSTs according to ZST resolution. The display module 335 displays both the ZSTs of the sensor signals and a color map to indicate regions of multiple resolution of the ZST. In some examples, a different resolution for each of the sensor signals 605 can be used in the display. The display module 335 may automatically create a color-coded map for the sensor signals 605 to indicate the multiple resolutions.

In some examples, the system 300 includes a memory in electrical communication with the processor 315 to store sensor data obtained from a plurality of sensor signals over at least one circadian cycle of the subject. The ZST module 320 calculates multi-resolution ZSTs over the sensor data obtained over the circadian cycle. This is useful to display ZSTs to show any variations of the sensor signals with circadian rhythms. For example, such a display may show that one or more sensor signals enter an outstanding region at a certain time of day.

According to some examples, the processor 315 includes a trending module. Sensor data received from one or more sensors and is stored in a memory. The trending module trends the sensor data and the ZST module 320 calculates a ZST of the trended sensor data. This is useful to identify physiologic cardiovascular events that may take some time to develop, such as heart failure decompensation for example. A ZST can be calculated over data for one or more sensors collected over days. A user can then zoom in on specific data segments through the user interface. This allows trend to be developed over prolonged periods such as a week-long period for example.

Figure 7:
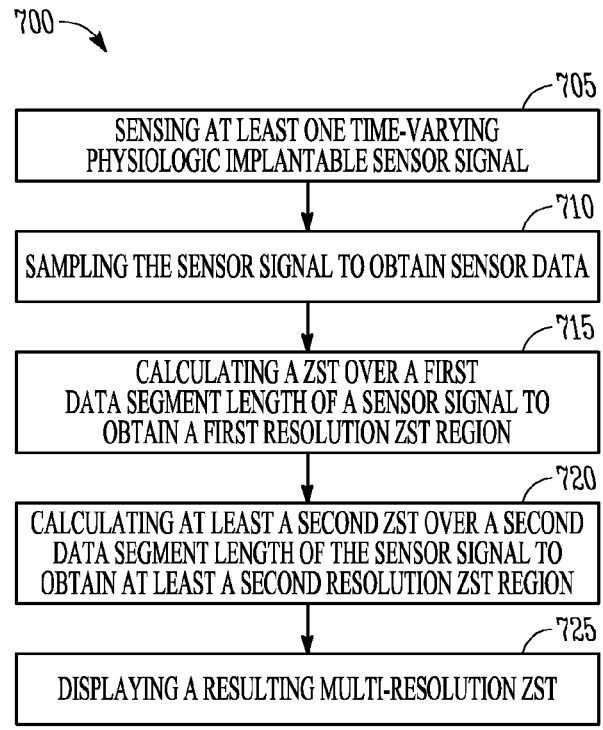
FIG. 7 shows a flow diagram of an example of a method to interpret data obtained from physiologic sensors.

FIG. 7 shows a flow diagram of an example of a method to interpret data obtained from physiologic sensors. At 705, at least one time-varying physiologic implantable sensor signal is sensed. At 710, the sensor signal is sampled to obtain sensor data. A multi-resolution ZST is then calculated for the sensor data. To calculate the multi-resolution ZST, a ZST is calculated over a first data segment length of a sensor signal to obtain a first resolution ZST region at 715, and at least a second ZST is calculated over a second data segment length of the sensor signal to obtain at least a second resolution ZST region at 720. At 725, a resulting multi-resolution ZST is displayed. In some examples, the second resolution ZST is calculated ZST when prompted through a user interface.

In some examples, the method 700 includes assigning a first display color-code to the first resolution ZST region and a second display color-code to the second resolution ZST region. Both the ZST of a sensor signal and one or more color-codes to indicate regions of multiple resolution of the ZST are displayed.

In some examples, a plurality of time-varying physiologic sensor signals is sensed. Multi-resolution ZSTs for the plurality of sensor signals are calculated and color-codes are assigned to multi-resolution regions of the ZSTs. Both the ZSTs of the sensor signals and a color map to indicate regions of multiple-resolution of the ZSTs are displayed.

In some examples, the method 700 includes assigning a first display color-code to a first region of the ZST and assigning a second display color-code to a second region of the ZST. The second region of the ZST includes at least one sensor data value that is outside of a predetermined normal value range. In some examples, the predetermined normal value range is ±2 standard deviations. Both the ZST and one or more color-codes are displayed to indicate one or more regions having a value outside the predetermined normal value range.

Figure 8:
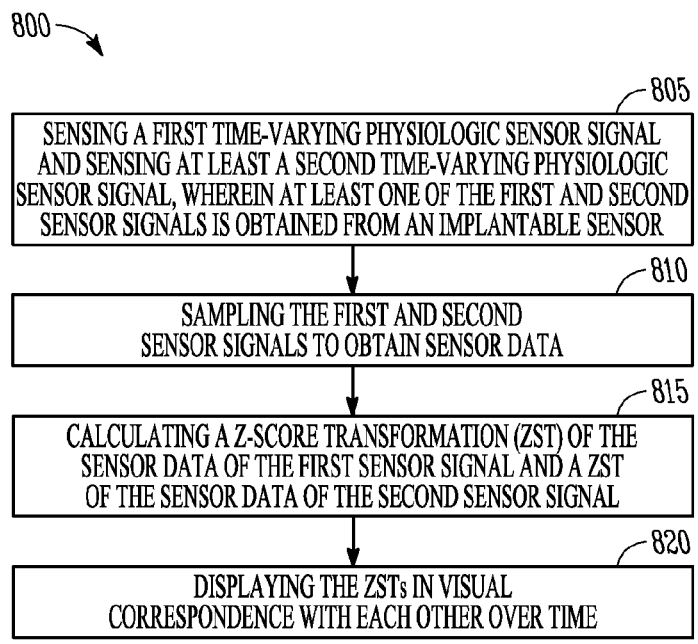
FIG. 8 shows a flow diagram of another example of a method to interpret data obtained from physiologic sensors.

FIG. 8 shows a flow diagram of another example of a method to interpret data obtained from physiologic sensors. At 805, a first time-varying physiologic sensor signal and at least a second time-varying physiologic sensor signal are sensed. In some examples, first sensor signal has a different scale from the second sensor signal with respect to time. In some examples, first sensor signal has a different scale from the second sensor signal with respect to data. In some examples, time-varying physiologic sensor signals are sensed from two or more sensors, and the sensor signals are related to physiologic cardiovascular events of a subject selected from, among other things, mean arterial pressure, stroke volume, heart rate, respiration rate, respiration volume, mechanical vibrations of the subject's heart, and activity of the subject.

At 810, the first and second sensor signals are sampled to obtain sensor data. At 815, a Z-score transformation (ZST) of the sensor data of the first sensor signal and a ZST of the sensor data of the second sensor signal are calculated. In some examples, a ZST is calculated over a sufficient amount of sensor data to record circadian variance of a sensor signal. In some examples, a ZST is recalculated in response to a signal received from a user interface. In some examples, a ZST is recalculated automatically when new sampled sensor data is available.

At 820, the ZSTs are displayed in visual correspondence with each other over time. In some examples, a first display color-code is assigned to a first region of a ZST and a second display color-code is assigned to a second region of the ZST. The second region of the ZST includes one or more sensor data values that are outside of a predetermined normal value range. The ZST of the sensor signal is displayed together with one or more color-codes to indicate one or more regions having a value outside the normal value range. In some examples, the method 800 includes trending the sensor data of at least one of the first and second sensor signals, calculating the ZST of trended sensor data, and displaying at least one ZST of the trended sensor data.

Figure 9:
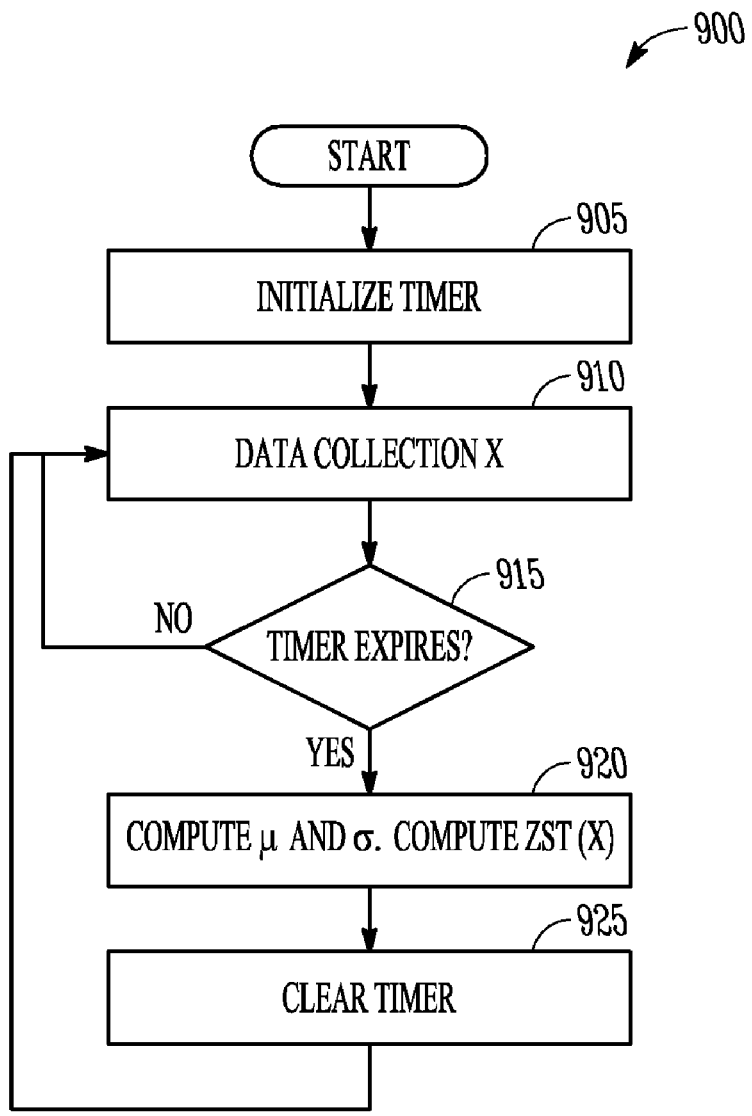
FIG. 9 shows a flow diagram of an example of a method of calculating a ZST offline.

In some examples, the sensor data is collected by an IMD and data is communicated to an external device at a later time. The ZST is calculated after all of the data is communicated. This can be referred to as an off-line ZST calculation. FIG. 9 shows a flow diagram of an example of a method 900 of calculating a ZST offline. At 905 a time is initialized. The timer times a duration for collecting data segment X which begins at 910. When the timer expires at 915, Z(X) is computed at 920 using Equation (1). The timer is cleared at 925 and the method 900 may resume collecting data or may wait for a signal generated by a detected event or a user before proceeding.

Figure 10:
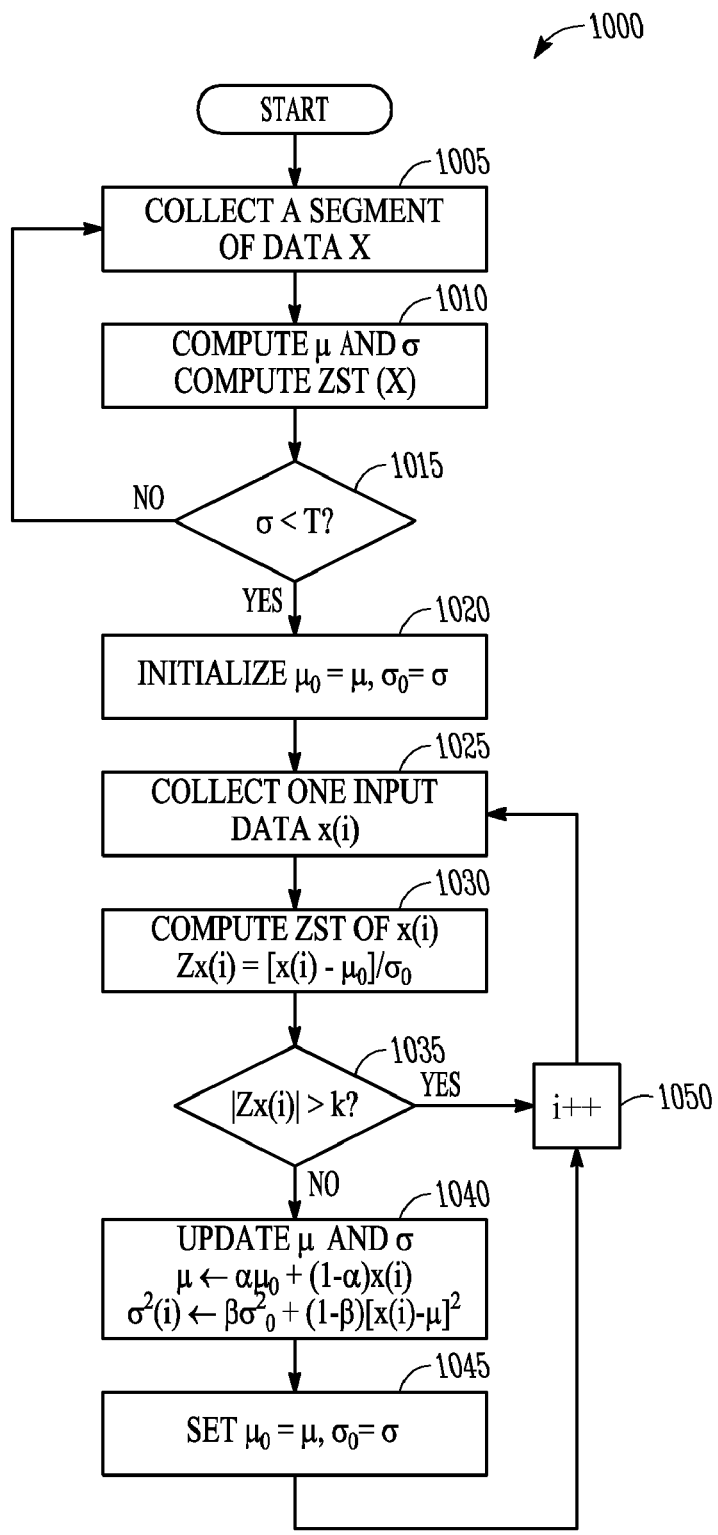
FIG. 10 shows a flow diagram of an example of a method of calculating a ZST in real time.

In some examples, the sensor data can be collected and communicated to an external device in real time. The ZST can be calculated as data becomes available. This can be referred to as a real time ZST calculation or a sequential ZST calculation. FIG. 10 shows a flow diagram of an example of a method 1000 of calculating a ZST in real time. At 1005, an initial segment of data is collected. At 1010, the mean μ and standard deviation σ and a ZST for the segment are computed. If the standard deviation σ is below a predetermined threshold T at 1015, the mean μ and standard deviation σ are initialized with the computed values at 1020. The threshold check ensures that the initial values are not calculated with outlier values. At 1025, one data input x(i) is collected when it becomes available. At 1030, the ZST is computed using x(i) according to $$Z_X(i):=(x(i)-\mu)/\sigma \quad (2).$$

At 1035, it is determined if the computed ZST is greater than a predetermined threshold k. Typically k is equal to two standard deviations, or k=2σ. If ZST is less than k, then new values for the mean μ and standard deviation σ are calculated at 1040. Otherwise, the index i is incremented at 1045 and the next data value is obtained at 1025. Also at 1040, the mean μ is calculated according to $$\mu = \alpha\mu_o + (1-\alpha) \times (i) \quad (3),$$

and the variance σ² is calculated according to $$\sigma^2 = \beta\sigma_o^2 + (1-\beta)[x(i)-\mu]^2 \quad (4).$$

The running values of $\mu_o$ and $\sigma_o$ are updated with the calculated values at 1045. The index i is incremented at 1050 and the next data value is obtained at 1025.

The examples of the methods described herein can be implemented in software. The software comprises computer executable instructions stored on computer readable media such as memory or other type of storage devices. This includes remote storage devices where the instructions are downloadable via the internet or other network to a machine for processing. Further, such methods may correspond to modules, which are software, hardware, firmware or any combination thereof. Multiple functions are performed in one or more modules as desired, and the embodiments described are merely examples. The software is executed on a digital signal processor, ASIC, microprocessor, or other type of processor, such as in a personal computer, server or other computer system.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A method comprising:
   sensing at least one time-varying physiologic sensor signal using an implantable sensor;
   sampling the sensor signal to obtain sensor data;
   calculating a multi-resolution Z-score transformation (ZST) of the sensor data by:
      calculating a ZST over a first data segment length of a sensor signal to obtain a first resolution ZST region; and
      calculating at least a second ZST over a second data segment length of the sensor signal to obtain at least a second resolution ZST region, wherein at least a portion of the second segment overlaps the first segment, and wherein the second resolution is different than the first resolution; and
   displaying the multi-resolution ZST.

2. The method of claim 1, including:
   assigning a first display color-code to a first region of the ZST;
   assigning a second display color-code to a second region of the ZST, wherein the second, region of the ZST includes a sensor data value that is outside of a predetermined normal value range; and
   displaying both the ZST of a sensor signal and one or more color-codes to indicate one or more regions having a value outside the predetermined normal value range.

3. The method of claim 2, wherein the predetermined normal value range is two standard deviations.

4. The method of claim 1, including:
   assigning a first display color-code to the first resolution ZST region and a second display color-code to the second resolution ZST region; and displaying both the ZST of a sensor signal and one or more color-codes to indicate regions of multiple resolution of the ZST.

5. The method of claim 4, including:
sensing a plurality of time-varying physiologic sensor signals;
calculating multi-resolution ZSTs for the plurality of sensor signals;
assigning color-codes to multi-resolution regions of the ZSTs; and
displaying both the ZSTs of the sensor signals and a color map to indicate regions of multiple-resolution of the ZSTs.

6. The method of claim 1, wherein calculating a multi-resolution Z-score transformation (ZST) includes:
calculating a ZST over a first data segment length of a sensor signal to obtain a first resolution ZST; and
calculating at least a second ZST over a second data segment length of the sensor signal to obtain at least a second resolution ZST when prompted through a user interface.

7. The method of claim 1, wherein calculating a multi-resolution ZST includes calculating a multi-resolution ZST when the processor determines that the ZST has a predetermined number of points outside a normal range.

8. The method of claim 1, wherein sampling the sensor signal to obtain sensor data occurs in real time and wherein calculating a ZST includes calculating the multi-resolution ZST while the sensor data is being obtained.

9. The method of claim 8, wherein calculating the ZST includes calculating a ZST $Z_x(i)$ in real time, when a new sensor datum $x(i)$ is obtained, according to $$Z_x(i):=(x(i)-\mu)/\sigma,$$

where $\mu$ represents a mean and $\sigma$ represents a standard deviation.

10. A method comprising:
sensing a first time-varying physiologic sensor signal and sensing at least a second time-varying physiologic sensor signal, wherein at least one of the first and second sensor signals is obtained from an implantable sensor;
sampling the first and second sensor signals to obtain first sensor data and second sensor data;
calculating a Z-score transformation (ZST) for the first sensor data and a ZST for the second sensor data including:
calculating a ZST over a first data segment length of at least one of the first or second sensor data to obtain a first resolution ZST region; and
calculating at least a second ZST over a second data segment length of the same first or second sensor data to obtain at least a second resolution ZST region wherein at least a portion of the second segment overlaps the first segment, and wherein the second resolution is different than the first resolution; and
displaying the ZSTs in visual correspondence with each other over time.

11. The method of claim 10, including:
assigning a first display color-code to a first region of a ZST;
assigning a second display color-code to a second region of the ZST, wherein the second, region of the ZST includes a sensor data value that is outside of a predetermined normal value range; and
displaying both the ZST of a sensor signal and one or more color-codes to indicate one or more regions having a value outside the predetermined normal value range.

12. The method of claim 10, including:
trending the sensor data, of at least one of the first and second sensor signals;
calculating the ZST of trended sensor data; and
displaying at least one ZST of the trended sensor data.

13. The method of claim 10, including sensing a plurality of time-varying physiologic sensor signals, wherein the plurality of sensor signals are related to physiologic cardiovascular events of a subject selected from the group consisting of:
mean arterial pressure;
stroke volume;
heart rate;
respiration rate;
respiration volume;
mechanical vibrations of the subject's heart; and
activity of the subject.

14. The method of claim 10, wherein calculating a ZST includes recalculating a ZST when new sampled sensor data is available.

15. The method of claim 10, wherein calculating ZST includes calculating a ZST over a sufficient amount of sensor data to record circadian variance of a sensor signal.

16. The method of claim 10, wherein sensing the first and second sensor signals includes sensing a first sensor signal having a different scale from the second sensor signal with respect to time.

17. The method of claim 10, wherein sensing the first and second sensor signals includes sensing a first sensor signal having a different scale from the second sensor signal with respect to data.

18. The method of claim 10, wherein displaying the ZSTs in visual correspondence with each other over time includes displaying different combinations of the ZSTs according to input received through a graphical user interface.

19. The method of claim 10, wherein displaying the ZSTs in visual correspondence with each other over time includes:
assigning a first display color-code to a ZST region having the first resolution and a second display color-code to a ZST region having the second resolution; and
displaying the ZST of a sensor signal and indicate regions of multiple resolution of the ZST using the color-codes.

20. The method of claim 10, wherein displaying the ZSTs in visual correspondence with each other over time includes displaying both the ZSTs of the sensor signals and a displaying color map to indicate regions of multiple resolution of the ZST.

* * * * *